(12) United States Patent
Toth et al.

(10) Patent No.: US 8,073,218 B2
(45) Date of Patent: Dec. 6, 2011

(54) METHOD FOR DETECTING BIO SIGNAL FEATURES IN THE PRESENCE OF NOISE

(75) Inventors: Michael S. Toth, Allentown, PA (US); Cecilia Anna Paulette Petit, Quakertown, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 686 days.

(21) Appl. No.: 12/284,999

(22) Filed: Sep. 25, 2008

(65) Prior Publication Data

US 2010/0074482 A1 Mar. 25, 2010

(51) Int. Cl.
*G06K 9/00* (2006.01)
(52) U.S. Cl. .......................................... 382/128; 382/243
(58) Field of Classification Search .................. None
See application file for complete search history.

(56) References Cited

U.S. PATENT DOCUMENTS

| | | | |
|---|---|---|---|
| 6,470,320 B1 | 10/2002 | Hildebrand et al. | |
| 6,533,724 B2 | 3/2003 | McNair | |
| 6,658,287 B1 * | 12/2003 | Litt et al. ...................... | 600/544 |
| 7,397,936 B2 * | 7/2008 | Periaswamy ................ | 382/128 |
| 2002/0099686 A1 | 7/2002 | Schwartz et al. | |
| 2003/0101076 A1 | 5/2003 | Zaleski | |
| 2004/0015337 A1 | 1/2004 | Thomas et al. | |
| 2004/0078232 A1 | 4/2004 | Troiani | |
| 2004/0103001 A1 | 5/2004 | Mazar et al. | |
| 2004/0236188 A1 | 11/2004 | Hutchinson et al. | |
| 2005/0119534 A1 | 6/2005 | Trost et al. | |
| 2006/0025931 A1 | 2/2006 | Rosen et al. | |
| 2006/0173663 A1 | 8/2006 | Langheier et al. | |
| 2006/0224416 A1 | 10/2006 | Lloyd et al. | |

* cited by examiner

*Primary Examiner* — Minh N Tang
(74) *Attorney, Agent, or Firm* — Willard Jones, II

(57) ABSTRACT

A computer-based method for detecting features in a digitally sampled biological (bio) signal includes the steps of applying a wavelet transform to the bio signal to generate a list of wavelet transform coefficients, ranking the coefficients according to value or frequency, and removing at least one low value or low frequency coefficient. The method further includes the steps of performing an inverse wavelet transform using the remaining coefficients to generate a reconstructed signal, and detecting feature locations using the reconstructed signal.

33 Claims, 15 Drawing Sheets

METHOD FOR DETECTING BIO SIGNAL FEATURES IN THE PRESENCE OF NOISE

BACKGROUND OF THE INVENTION

This invention relates to methods for detecting signal features from a biological (bio) signal in the presence of noise.

An electrocardiogram (ECG or EKG), is a graphic produced by an electrocardiograph, which records the electrical activity (a signal) of the heart over time. Electrical waves cause the heart muscle to pump. These waves pass through the body and can be measured at electrodes (electrical contacts) attached to the skin. Electrodes on different sides of the heart measure the activity of different parts of the heart muscle. An EKG displays the voltage (a signal) between pairs of these electrodes, and the muscle activity that they measure, from different directions. This display indicates the overall rhythm of the heart, and weaknesses in different parts of the heart muscle. It is a way to measure and diagnose abnormal rhythms of the heart, particularly abnormal rhythms caused by damage to the conductive tissue that carries electrical signals, or abnormal rhythms caused by levels of salts, such as potassium, that are too high or low.

The ability to analyze an EKG signal and detect variances therein, provides the ability to monitor the physiological condition of a heart. For instance, accurate detection of variances in an EKG signal allows for the detection of heart events, such as heartbeat detection, arrhythmias, ischemias, and a myriad of other events. To detect variances in the EKG signal, it is necessary to minimize or eliminate noise, which also causes variances in an EKG signal, but does not correspond to a physiological event of the heart. Otherwise, the noise variance may be misconstrued as a heart event. In turn, this can lead to a potential misdiagnosis, false positive, missed event, or failure to detect other rhythms; among other undesirable results. In particular, noise can lead to false identification of R waves, resulting in the detection of more heartbeats than what actually occurred. Misidentification may occur when, for example, baseline drift is present in the signal.

One known method of removing low frequency noise involves using a low pass filter followed by a length transform, which computes the length of a curve within a given time window. When the length exceeds a predetermined threshold, the curve is identified as being an R wave. When baseline drift is present, portions of the curve that should be flat are instead sloped. This may increase the calculated curve length and lead to misidentification of the curve as an R wave.

In addition, baseline drift may add noise to the length transform, reducing the transform's definition and therefore causing a failure to perceive smaller peaks, which results in underreporting of R waves. Accordingly, a need exists for techniques which are able to detect heartbeats, along with signal features of other bio signals (such as brain waves), in the presence of noise.

BRIEF SUMMARY OF THE INVENTION

A first example embodiment of the present invention relates to a computer-based method for detecting features in a digitally sampled bio signal. The method includes the steps of applying a wavelet transform to the bio signal to generate a list of wavelet transform coefficients, ranking the coefficients according to value, and removing at least one low value coefficient. The method further includes the steps of performing an inverse wavelet transform using the remaining coefficients to generate a reconstructed signal, and detecting feature locations using the reconstructed signal.

A second example embodiment of the present invention relates to a computer-based method for detecting features in a digitally sampled bio signal. The method includes the steps of applying a wavelet transform to the bio signal to generate a list of wavelet transform coefficients, ranking the coefficients according to frequency, and removing at least one low frequency coefficient. The method further includes the steps of performing an inverse wavelet transform using the remaining coefficients to generate a reconstructed signal, and detecting feature locations using the reconstructed signal.

A third example embodiment of the present invention relates to a device for detecting features in a digitally sampled bio signal. The device includes a communications arrangement configured to receive the bio signal, a processor, and a memory. The memory includes instructions configuring the processor to apply a wavelet transform to the bio signal to generate a list of wavelet transform coefficients, rank the coefficients according to value, and remove at least one low value coefficient. The instructions further configure the processor to perform an inverse wavelet transform using the remaining coefficients to generate a reconstructed signal, and detect feature locations using the reconstructed signal.

A fourth example embodiment of the present invention relates to a device for detecting features in a digitally sampled bio signal. The device includes a communications arrangement configured to receive the bio signal, a processor, and a memory. The memory includes instructions configuring the processor to apply a wavelet transform to the bio signal to generate a list of wavelet transform coefficients, rank the coefficients according to frequency, and remove at least one low frequency coefficient. The instructions further configure the processor to perform an inverse wavelet transform using the remaining coefficients to generate a reconstructed signal, and detect feature locations using the reconstructed signal.

A fifth example embodiment of the present invention relates to a computer-readable medium having stored thereon a series of instructions executable by a processor for detecting features in a digitally sampled bio signal. The instructions are configured to cause the processor to perform the steps of applying a wavelet transform to the bio signal to generate a list of wavelet transform coefficients, ranking the coefficients according to value, and removing at least one low value coefficient. The instructions are further configured to cause the processor to perform the steps of performing an inverse wavelet transform using the remaining coefficients to generate a reconstructed signal, and detecting feature locations using the reconstructed signal.

A sixth example embodiment of the present invention relates to a computer-readable medium having stored thereon a series of instructions executable by a processor for detecting features in a digitally sampled bio signal. The instructions are configured to cause the processor to perform the steps of applying a wavelet transform to the bio signal to generate a list of wavelet transform coefficients, ranking the coefficients according to frequency, and removing at least one low frequency coefficient. The instructions are further configured to cause the processor to perform the steps of performing an inverse wavelet transform using the remaining coefficients to generate a reconstructed signal, and detecting feature locations using the reconstructed signal.

DETAILED DESCRIPTION OF THE INVENTION

The present invention relates to detecting features of bio signals in the presence of noise, such as baseline drift. An example system and methods will be described below with reference to the detection of heartbeats in an EKG signal. The example system and methods may be implemented in hardware, software, or a combination thereof.

Figure 1:
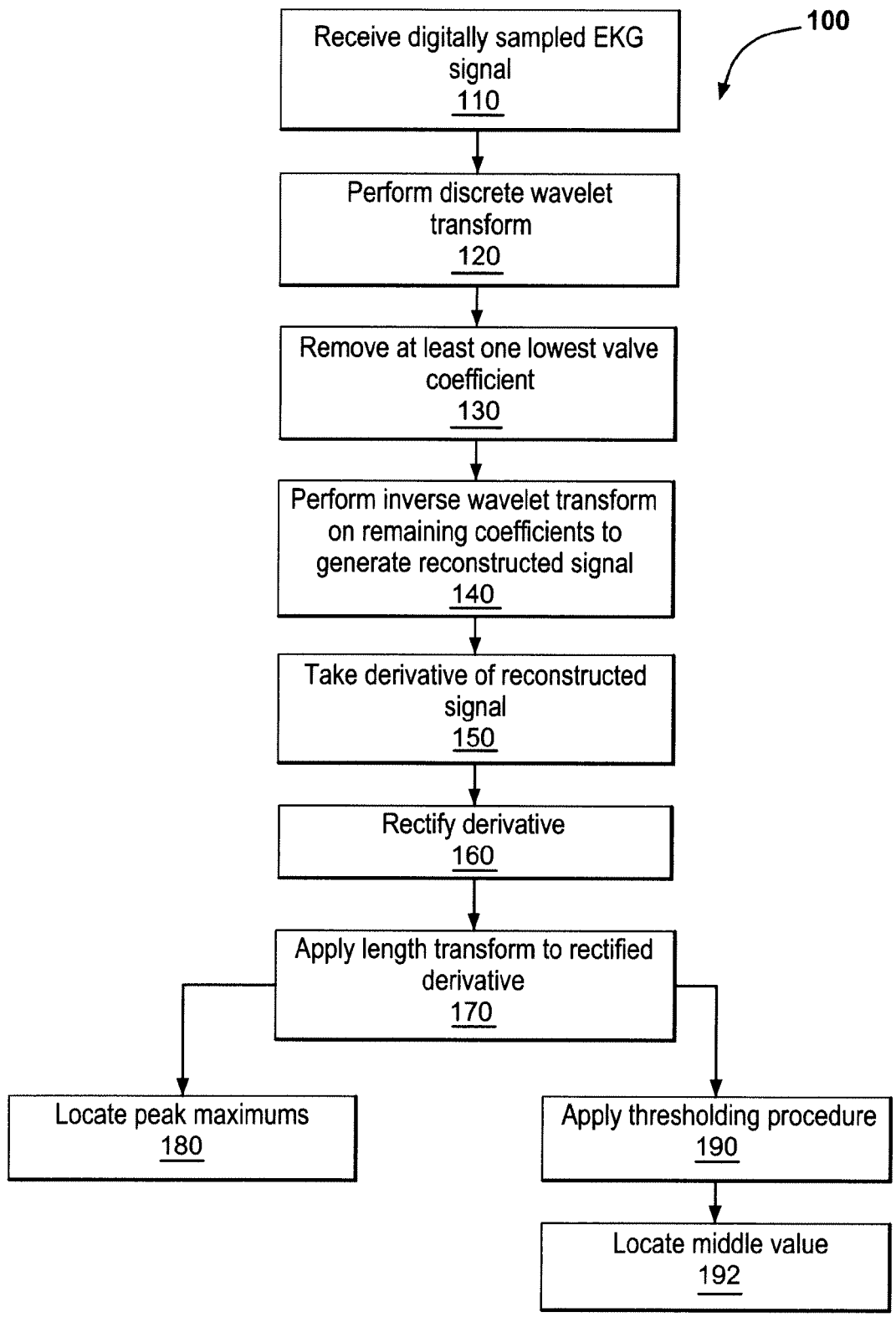
FIG. 1 shows an example of a method for detecting bio signal features in the presence of noise according to an example embodiment of the present invention.
Figure 2:
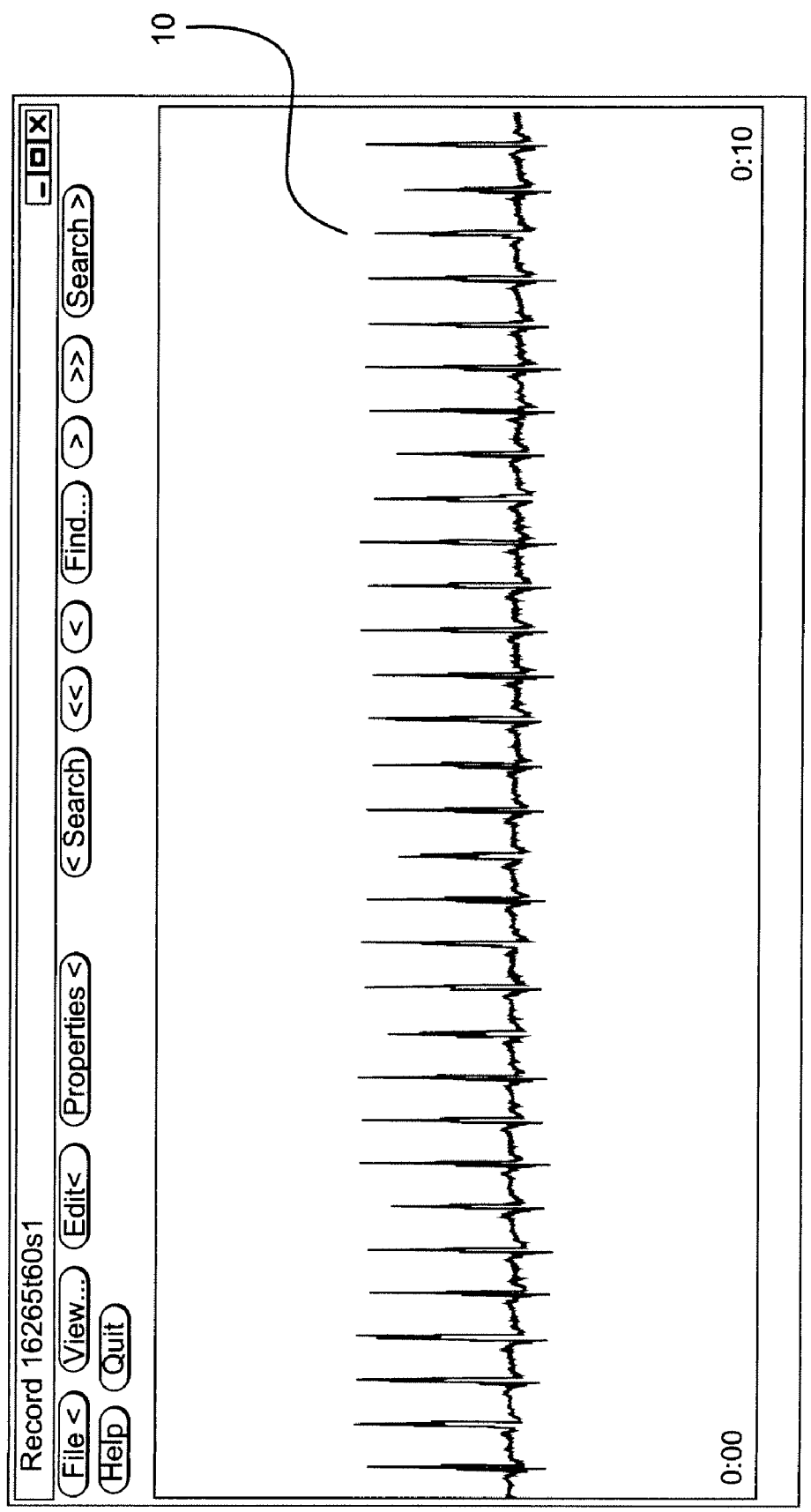
FIG. 2 shows an example of a digitally sampled bio signal.

FIG. 1 shows an example of a method 100 for detecting bio signal features (heartbeats) in the presence of noise according to an example embodiment of the present invention. In 110, a digitally sampled EKG signal may be received, e.g., in a computing device performing the method 100. When an analog signal is sampled, it can be converted into digital form using an analog-to-digital converter. The EKG signal may be stored as an array of voltage values, each associated with a corresponding time value. Other storage structures are also possible. An example of an EKG signal 10 is shown in FIG. 2. The EKG signal 10 includes periodic spikes (e.g., R waves) which may correspond to heartbeats. However, differentiating noise from actual heartbeats using conventional techniques may be difficult since noise and R waves may be of similar frequency and magnitude.

In 120, a discrete wavelet transform may be performed on the EKG signal. A mathematical procedure may be performed in which a wavelet function, such as a Haar wavelet or a Daubechies wavelet is scaled (dilated) and translated to produce secondary wavelets. The secondary wavelets may be combined to transform a time-based function, e.g., the EKG signal, into a series of time-frequency representations of the original function, known as a wavelet series decomposition. Wavelet transforms are advantageous compared to Fourier transforms because the original function is represented in terms of both time and frequency, enabling analysis of the function's behavior over both domains. The wavelet transform of the EKG signal may be represented as a two-dimensional matrix, where one dimension represents time, the other dimension represents scale, and a value of each entry represents the prevalence of features in the EKG signal that occur at a time and scale corresponding to the entry.

In 130, at least one lowest value coefficient is removed from consideration. It may be desirable to remove the lowest value components in order to focus on more prevalent signal features. It may be preferable to remove as many low value components as possible. However, removing too many coefficients may result in detection errors. Thus, the number of high value coefficients to retain may be critical to detection accuracy. As will be discussed below, an iterative technique may be utilized to select the high value coefficients to be retained.

Figure 3:
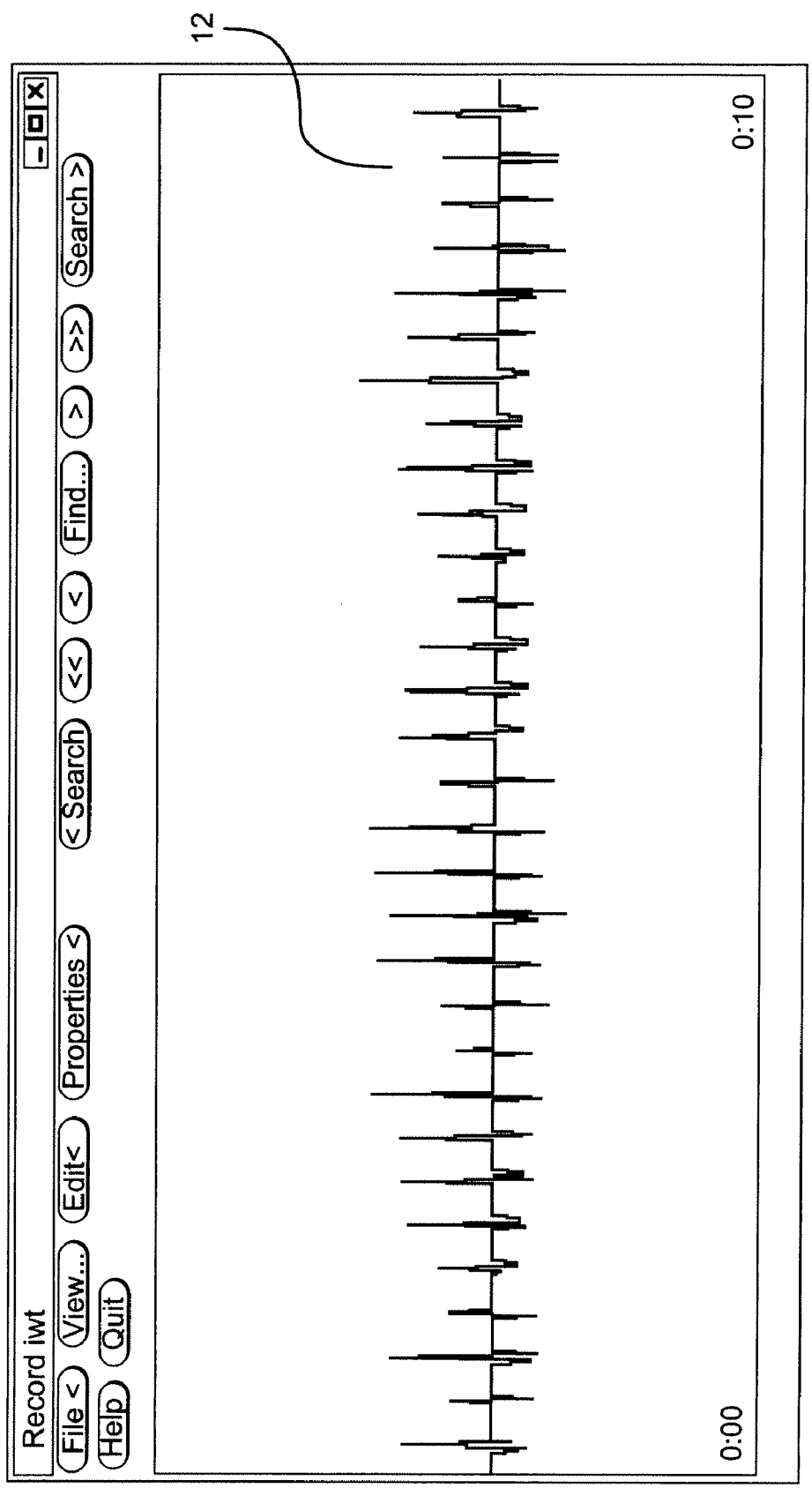
FIG. 3 shows the signal of FIG. 2 after performing an inverse wavelet transform using high value coefficients according to an example embodiment of the present invention.

In 140, an inverse wavelet transform may be performed on the coefficients that remain after removing the low value coefficient(s). The inverse transform may generate a reconstructed version of the EKG signal, except that the features corresponding to the removed coefficients may no longer be present. The reconstructed signal, similar to the EKG signal, may be represented as a time-based function, e.g., as a one-dimensional array of values. FIG. 3 shows a reconstructed signal 12, which represents the signal 10 after performing an inverse wavelet transform using only high value coefficients. As seen in FIG. 3, the spikes are substantially preserved while low frequency components have been removed. This is illustrated by a flatness of the reconstructed signal 12 between each spike.

Figure 4:
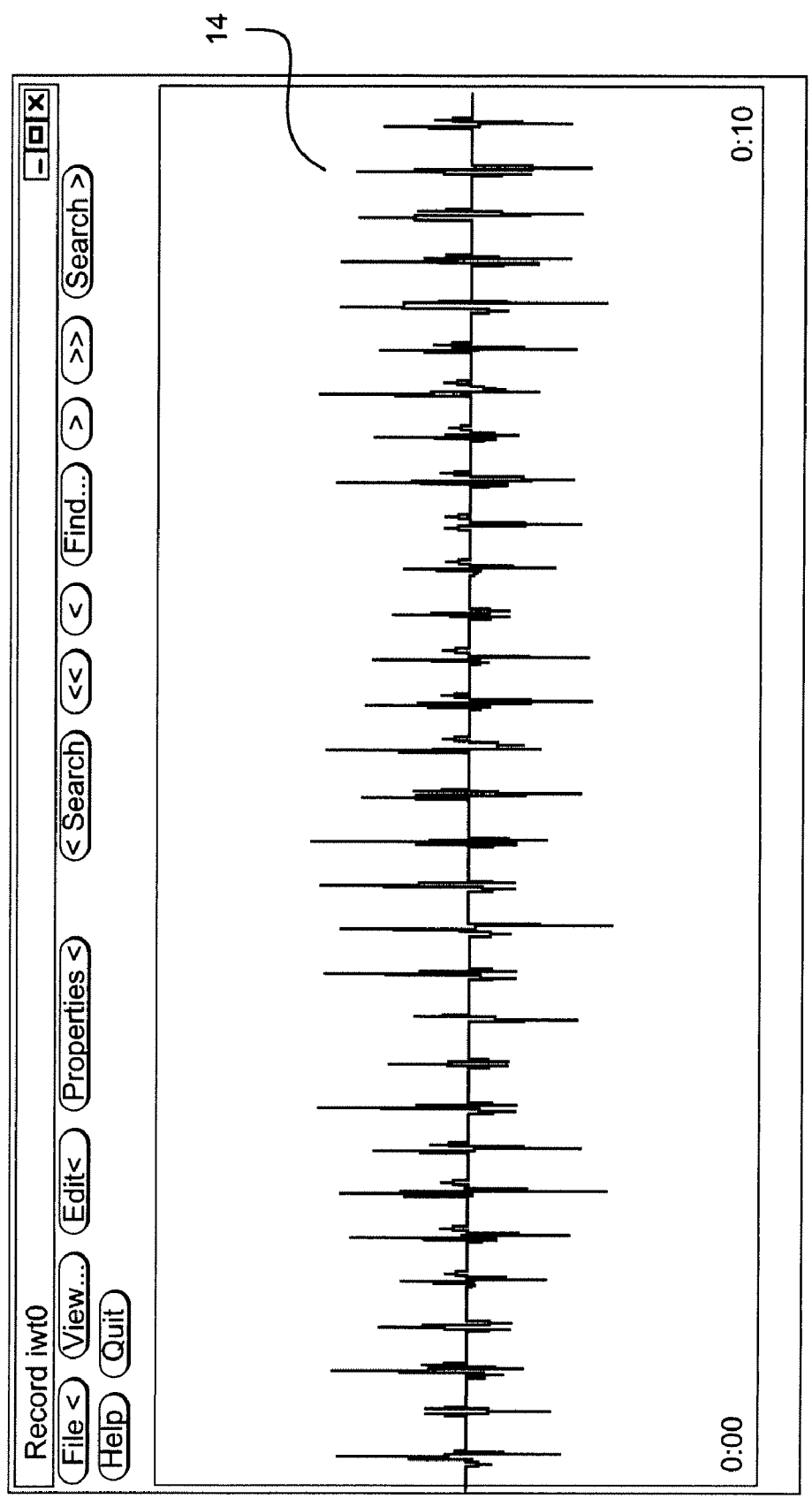
FIG. 4 shows the signal of FIG. 3 after performing a derivative operation according to an example embodiment of the present invention.

In 150, a mathematical derivative of the reconstructed signal may be taken. The derivative may amplify spikes in the reconstructed signal, since spikes have high derivative values. Although taking the derivative may be advantageous, it is optional and, in other embodiments, the taking of the derivative may not be performed. FIG. 4 shows a derivative signal 14, which represents a derivative of the reconstructed signal 12. The derivative signal 14 may include spikes in both the positive and negative directions, respectively indicating sharp upwards and downwards transitions in the reconstructed signal 12.

Figure 5:
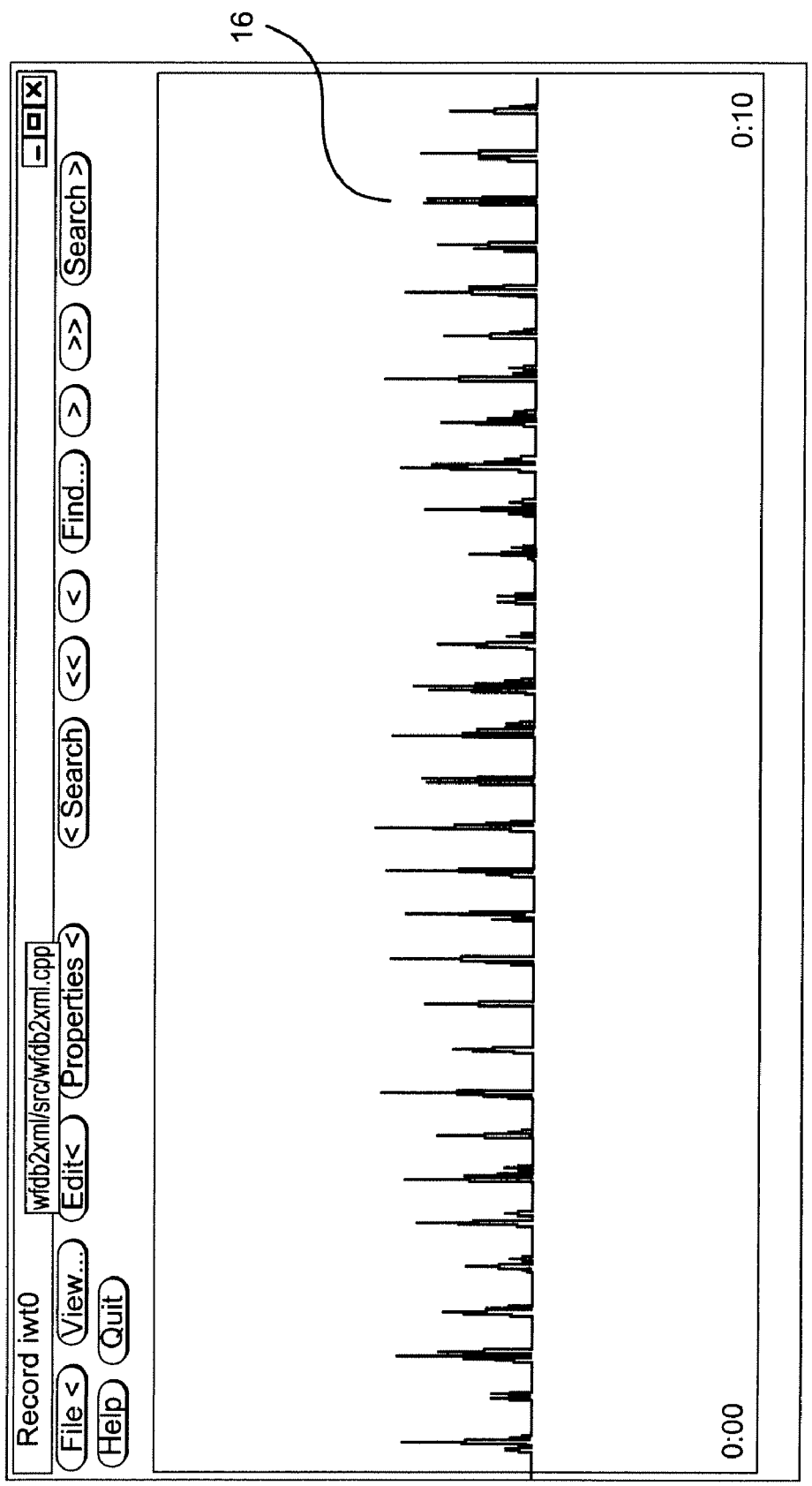
FIG. 5 shows the signal of FIG. 4 after performing signal rectification according to an example embodiment of the present invention.

In 160, the derivative signal may be rectified. Rectification converts negative values into positive values and may be used to simplify signal analysis. FIG. 5 shows a rectified signal 16, which represents the derivative signal 14 after being rectified. As seen in FIG. 5, rectification may produce a series of spikes grouped closely together. Each group may indicate the location of a heartbeat.

In 170, a length transform may be applied to the rectified derivative. Length transforms are a mathematical operation in which a sliding window is passed through a function, e.g., the rectified signal. The intersection of the function with the window as it slides across the function may determine the output of the length transform. The length transform may smooth the rectified signal by grouping together peaks that are near each other. A size of the window may affect the smoothing ability of the length transform. If the window size is too small, not enough smoothing may occur and peaks may not be grouped together. If the window size is too large, peaks which are not located near each other may be grouped together. That is, a large window size may result in the combining of different heartbeats.

Figure 6:
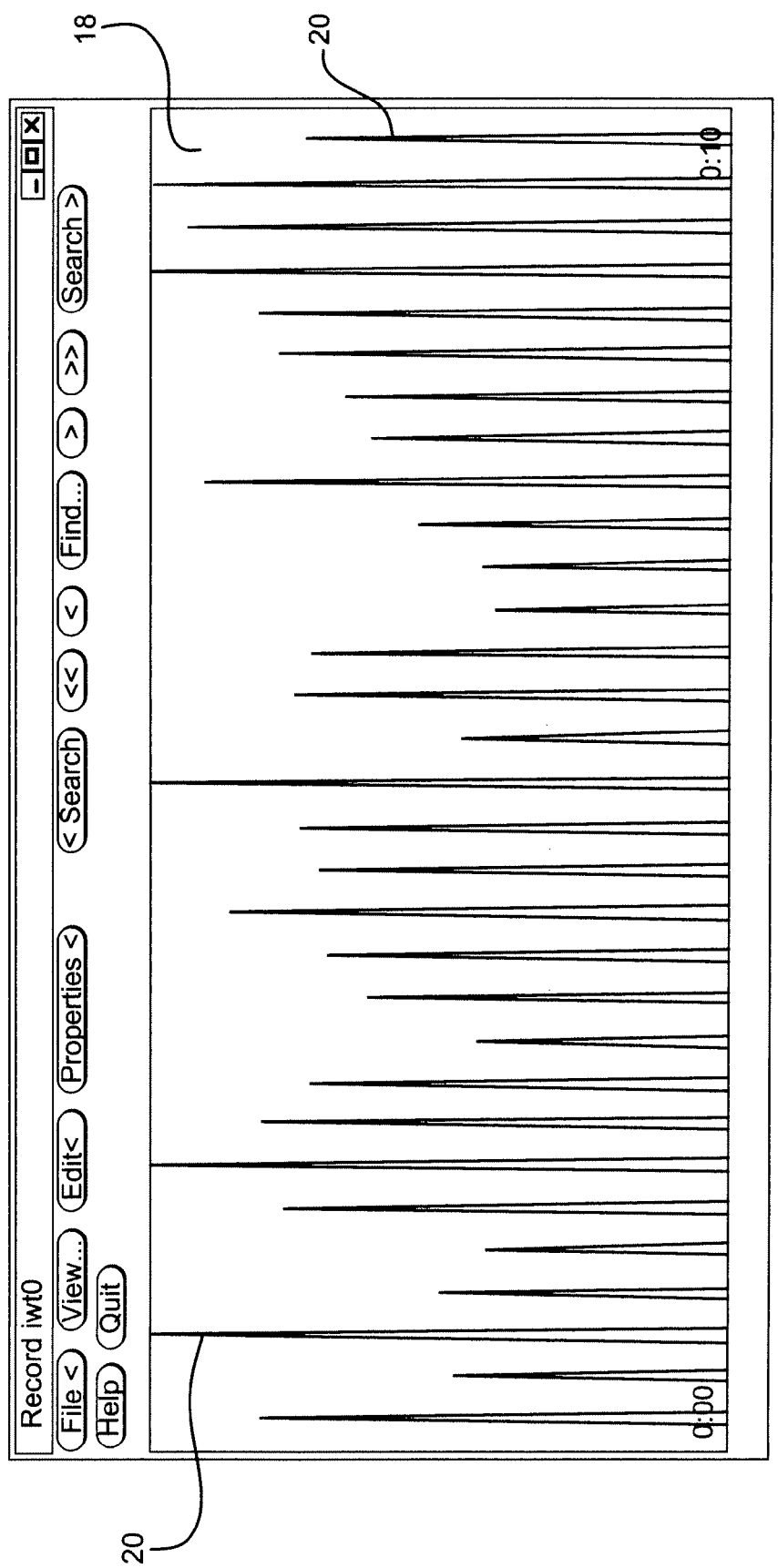
FIG. 6 shows the signal of FIG. 5 after performing a length transform according to an example embodiment of the present invention.

The selection of the window size may be influenced by the periodic nature of the function being analyzed. For instance, human heartbeats are generally spaced one second apart, i.e., sixty beats per minute. Based on this fact, a default window size may be ten percent of one second. The default window size may also be adjusted according to each individual. For example, athletes often have lower heart rates than the rest of the population, so data recorded from an athlete may be subjected to a larger window size, since there is less risk of combining heartbeats. FIG. 6 shows a transformed signal 18 which includes peaks 20 and represents a length transform of the rectified signal 16.

After the length transform is applied, heartbeat locations may be determined by, for example, locating peak maximums (180) or applying a thresholding procedure (190). In 180, peak maximums may be located by taking a derivative of the transformed signal and determining locations where the derivative goes from positive to negative. Another technique for locating peak maximums may be to evaluate the slope of the transformed signal directly to determine when the slope changes direction.

Figure 7:
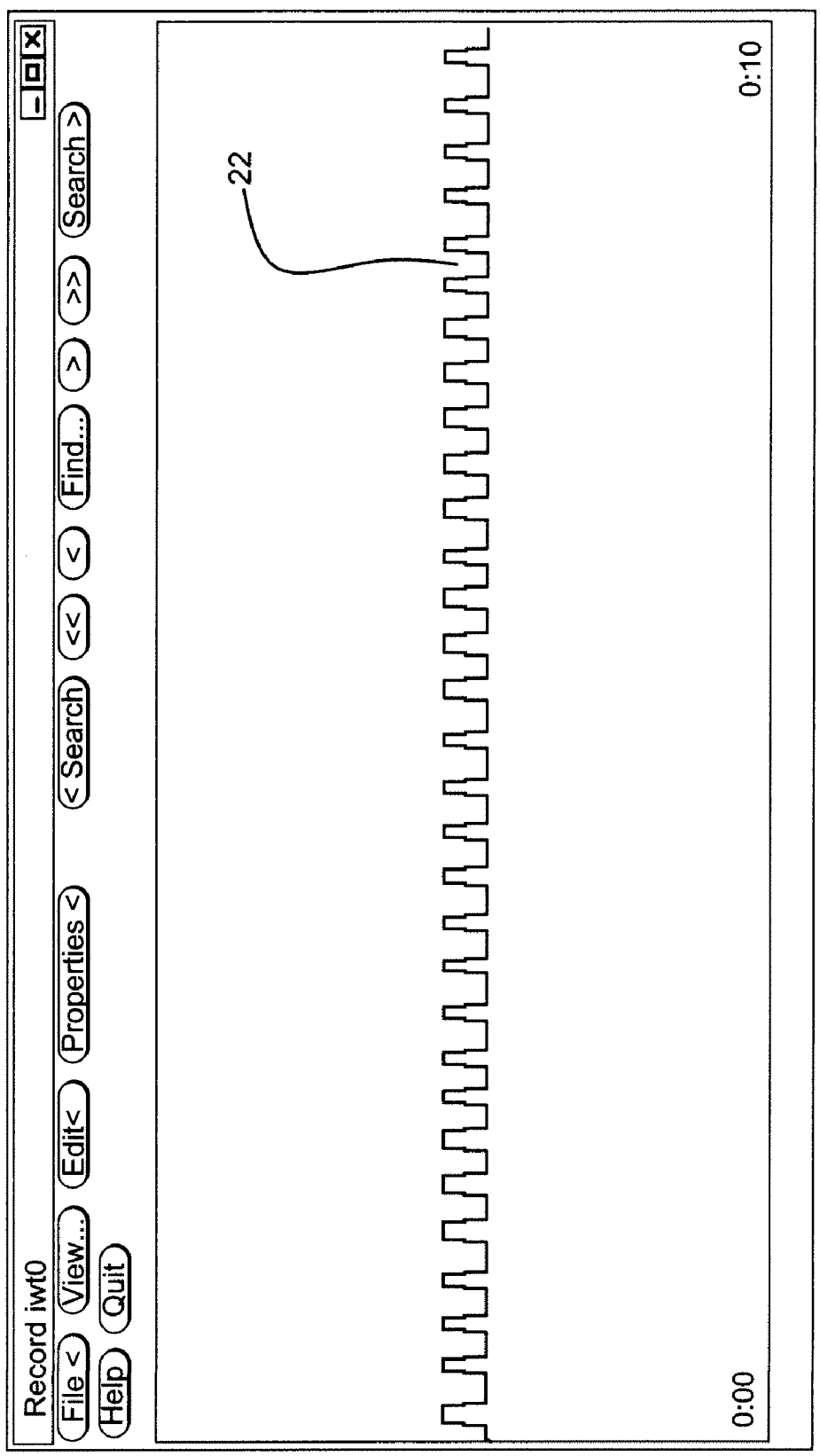
FIG. 7 shows the signal of FIG. 6 after performing thresholding according to an example embodiment of the present invention.

In 190 a thresholding procedure may be performed by limiting the maximum value of the transformed signal. A cutoff value may be determined as a function of the maximum value of any peak. For example, the cutoff value may be half of the maximum value. Signal values exceeding the cutoff value may be converted into the cutoff value. FIG. 7 shows a thresholded signal 22, which represents the transformed signal 18 after applying thresholding. As seen in FIG. 7, thresholding may flatten each peak to produce a substantially square wave.

In 192, heartbeat locations may be determined by locating middle values of the thresholded signal. One technique for locating middle values is to take the middle value between endpoints of the base of each square wave. That is, taking half the distance from a beginning of a peak pulse to an end of the peak pulse. However, in an alternative embodiment, the middle value may be located as a function of the maximum value. Starting with a left portion of a peak, a point may be located which has a value which is a function of the maximum value. In one embodiment, the function may be simply half the maximum value, e.g., the cutoff value. A similarly valued point may be located on a right portion of the same peak. The distance between the two points may be determined and the middle value selected to be half the distance.

Figure 8:
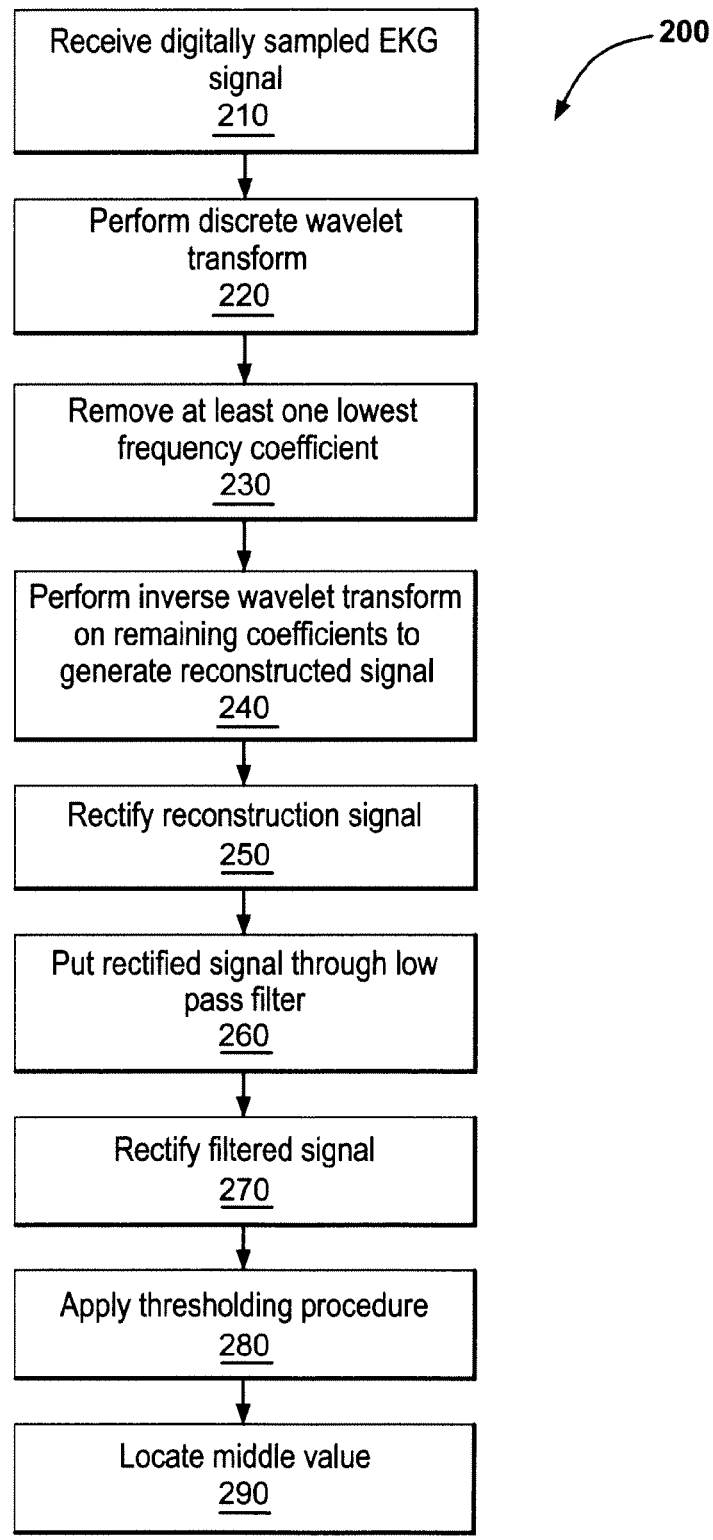
FIG. 8 shows an example of another method for detecting bio signal features in the presence of noise according to an example embodiment of the present invention.

FIG. 8 shows an example of a method 200 for detecting bio signal features (heartbeats) in the presence of noise according to an example embodiment of the present invention. In 210, a digitally sampled EKG signal may be received. In 220, a discrete wavelet transform may be performed on the EKG signal. The receiving and the wavelet transform may be performed in a manner substantially similar to that described above with reference to 110 and 120 of the method 100.

In 230, at least one lowest frequency coefficient is removed from consideration. Since wavelet transforms are scaled, the number of entries in each row of the two-dimensional matrix representing the wavelet transform may vary. For instance, if scaling is dyadic, then a first row of the matrix (representing the lowest frequencies) may have $2^1=2$ entries, a second row (representing higher frequencies) may have $2^2=4$ entries, a third row may have $2^3=8$ entries, etc. Coefficients may be removed either individually, e.g., going across each row one-by-one, or as a group, e.g., removing entire rows at a time. As discussed above, baseline drift occurs at low frequencies. Accordingly, it may be desirable to remove as many low frequency coefficients are possible while still providing accurate results. As will be discussed below, an iterative technique may be utilized to select the high frequency coefficients to be retained.

Figure 9:
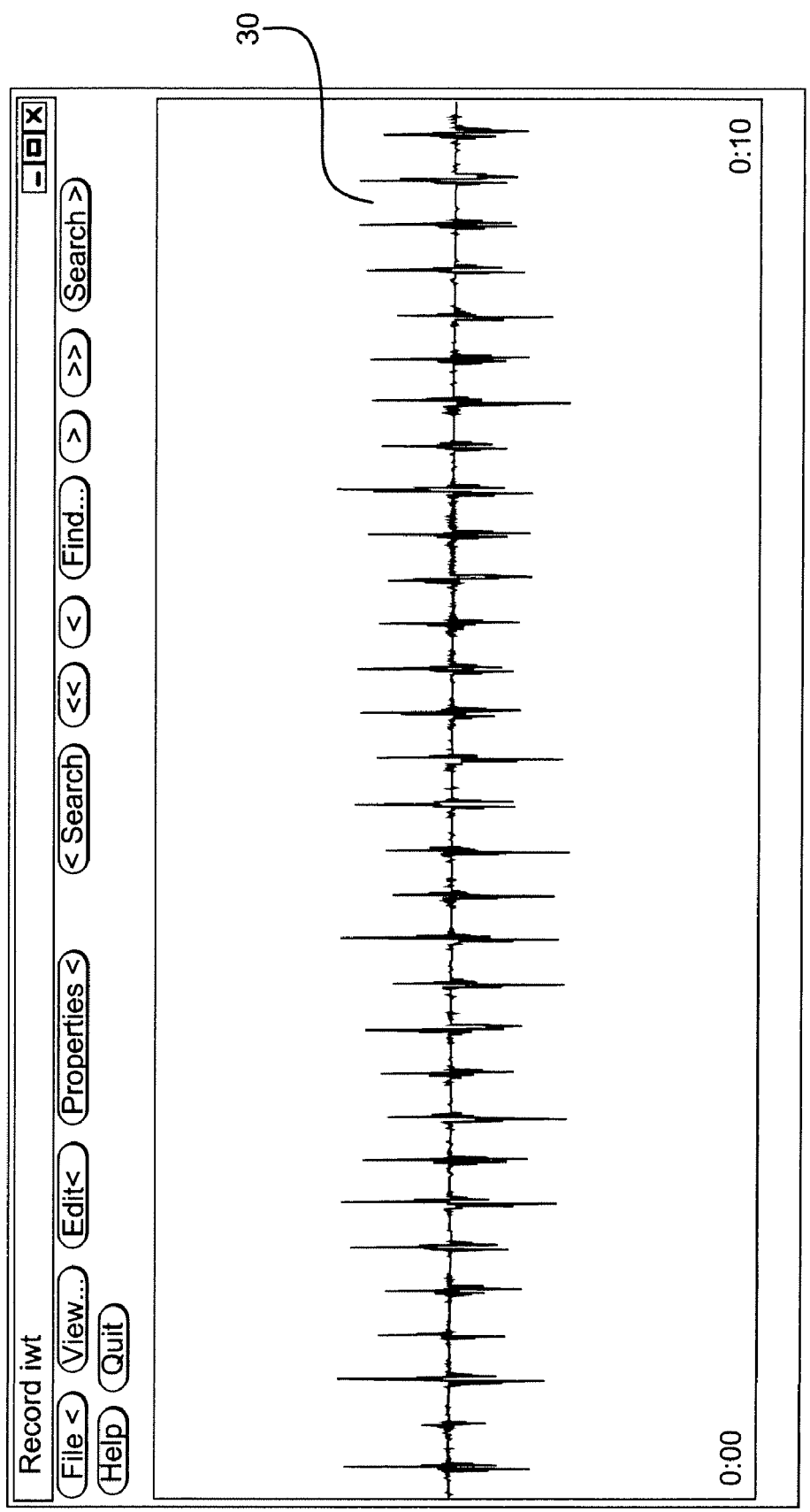
FIG. 9 shows the signal of FIG. 2 after performing an inverse wavelet transform using high frequency coefficients according to an example embodiment of the present invention.

In 240, an inverse wavelet transform may be performed on the coefficients that remain after removing the low frequency coefficient(s). The inverse transform may generate a reconstructed version of the EKG signal, except that the features corresponding to the removed coefficients may no longer be present. FIG. 9 shows a reconstructed signal 30, which represents the signal 10 after performing an inverse wavelet transform using only high frequency coefficients.

In 250, the reconstructed signal may be rectified so that negative values are converted into positive values. Although rectification of the reconstructed signal may not be necessary, it may be preferable to perform signal analysis on only positive values.

In 260, the rectified signal may be filtered through a low pass filter, e.g., a low pass box car.

Figure 10:
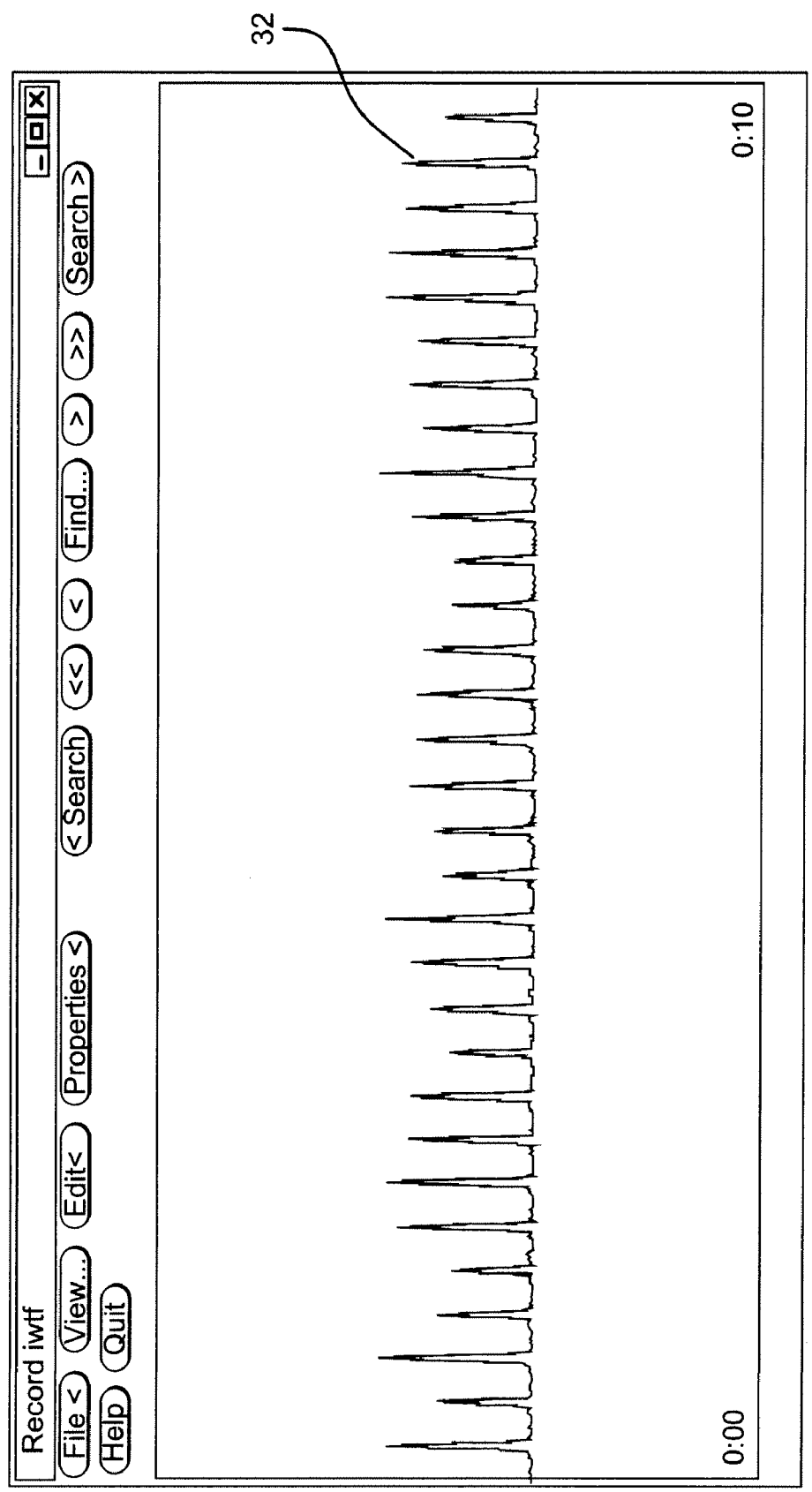
FIG. 10 shows the signal of FIG. 9 after performing filtering and rectification according to an example embodiment of the present invention.

In 270, the filtered signal may be rectified. This step may not be necessary if the reconstructed signal was rectified prior to filtering. Rather, it will be appreciated that rectification can occur after filtering instead of before. While rectifying prior to filtering may yield similar final results compared to rectifying after filtering, it should be noted that intermediate results of both types of filtering may differ. That is to say that a rectified reconstructed signal may differ slightly from a rectified filtered signal, but not to the extent of affecting the number of heartbeats detected in either case. FIG. 10 shows a filtered and rectified signal 32, which represents the reconstructed signal 30 after being rectified and low pass filtered.

Figure 11:
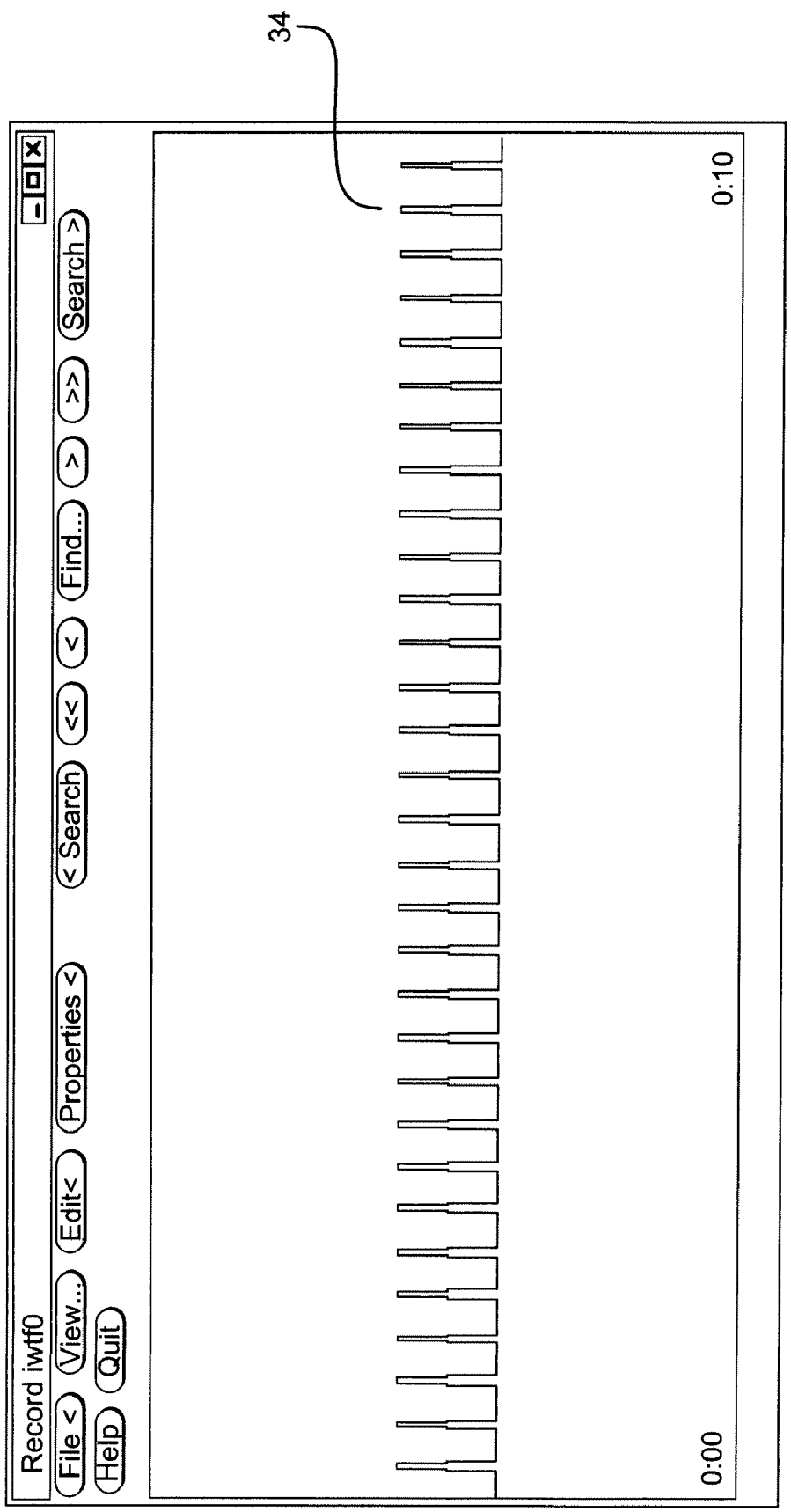
FIG. 11 shows the signal of FIG. 10 after performing thresholding according to an example embodiment of the present invention.

In 280, a thresholding procedure may be applied to the filtered and rectified signal. In 290, a middle value corresponding to a heartbeat may be located. The thresholding procedure and the locating of the middle value may be performed in a manner similar to that described above with reference to steps 190 and 192 of the method 100. FIG. 11 shows a thresholded signal 34, which represents the filtered and rectified signal 32 after thresholding.

Although the method 200 has been described with reference to the detection of heartbeats using thresholding/middle value location, it will be appreciated that detection may also be performed using peak detection as previously described with reference to the method 100. Either procedure may be used.

Figure 12:
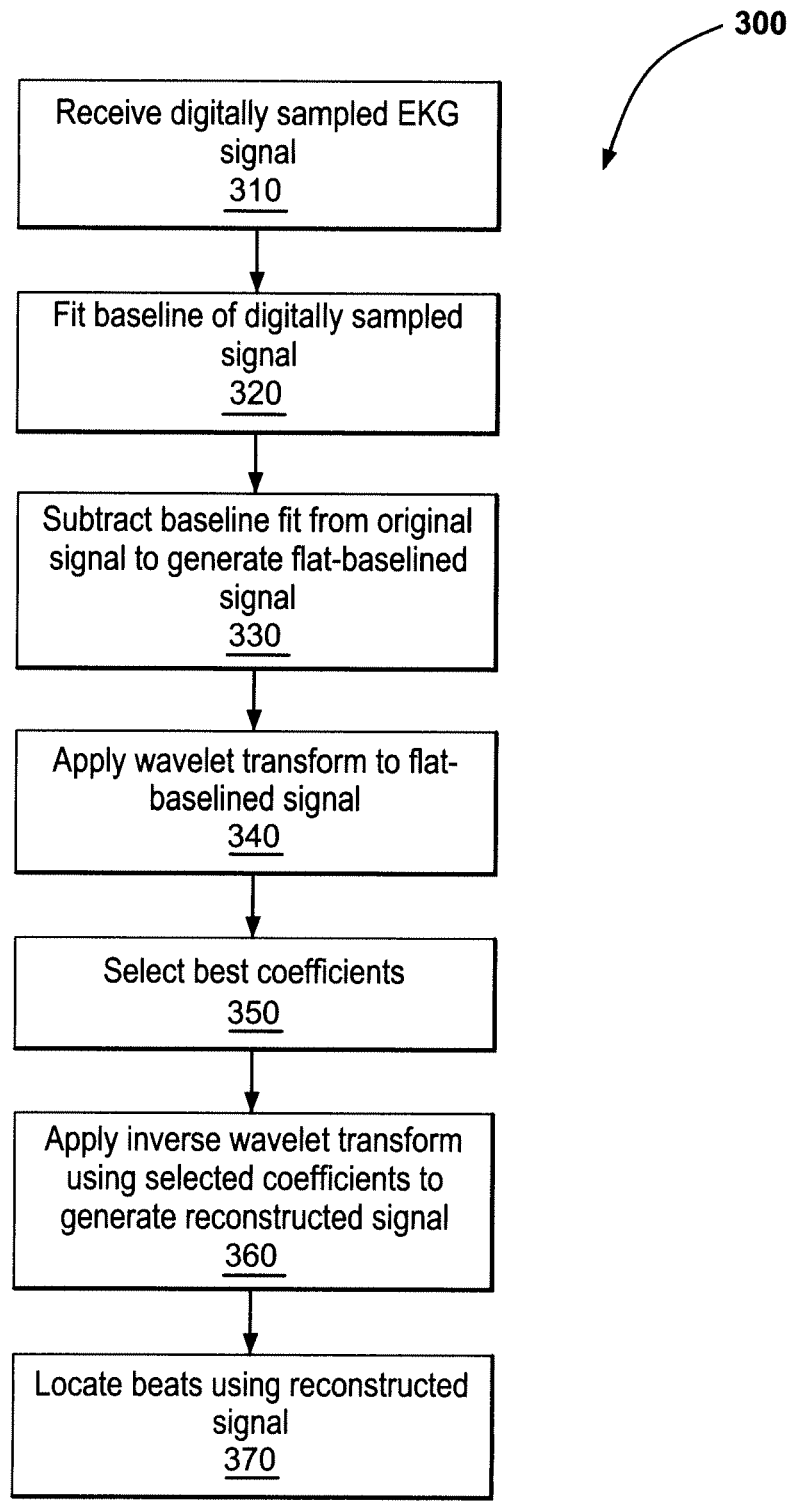
FIG. 12 shows an example of another method for detecting bio signal features in the presence of noise according to an example embodiment of the present invention.

FIG. 12 shows an example of a method 300 for detecting bio signal features (heartbeats) in the presence of noise according to an example embodiment of the present invention. In 310, a digitally sampled EKG signal may be received.

In 320, a baseline of the EKG signal may be fitted using, for example, a polynomial function.

In 330, the baseline fit may be subtracted from the EKG signal to generate a flat-baselined signal. The fitting and subtracting may be performed in accordance with a technique described in U.S. patent application Ser. No. 12/284,932 titled Method for Reducing Baseline Drift in a Biological Signal, (in name of Toth et al) filed even date herewith, the entire disclosure of which is hereby incorporated by reference, and which describes a method for removing baseline drift by fitting a piecewise cubic function to the baseline of a bio signal and subtracting the cubic function from the bio signal.

In 340 a discrete wavelet transform may be applied to the flat-baselined signal to form a two-dimensional array of coefficients.

In 350, the best coefficients may be selected to be retained. As discussed above, coefficients may be selected based on value or frequency. Unselected coefficients may be removed from further consideration.

In 360, an inverse wavelet transform may be applied to the selected coefficients to generate a reconstructed signal.

In 370, heartbeat locations may be located using the reconstructed signal, e.g., by detecting peak maximums or using a combination of thresholding and middle value location.

Exemplary embodiments of methods for selecting coefficients to retain will now be described. The example coefficient selecting methods may be used in conjunction with any of the methods 100, 200 and 300 previously described.

Figure 13:
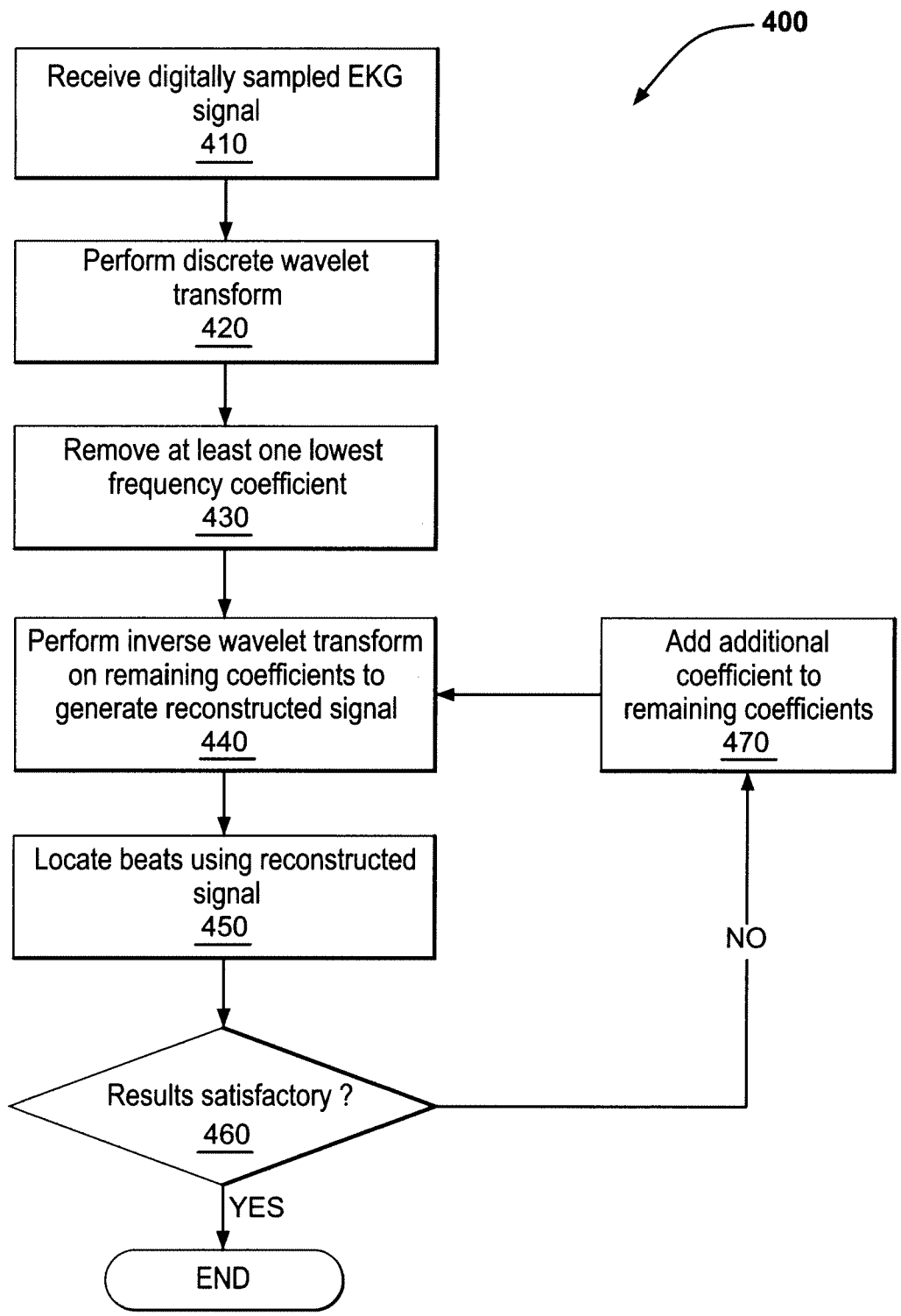
FIG. 13 shows an example of a method for selecting wavelet coefficients according to an example embodiment of the present invention.

FIG. 13 shows an example of a method 400 for selecting wavelet coefficients according to an example embodiment of the present invention. In 410, a digitally sampled EKG signal may be received.

In 420, a discrete wavelet transform may be performed using the EKG signal.

In 430, all but one row of coefficients, e.g., the row with the highest value or the highest frequency coefficients, may be removed. A single set of remaining coefficients may serve as initial coefficients for an iterative coefficient selection process, as described below.

In 440, an inverse wavelet transform may be performed on the remaining coefficients to generate a reconstructed signal.

In 450, heartbeat locations may be determined, e.g., using peak maximums or thresholding/middle value location, on the reconstructed signal.

In 460, a determination may be performed whether results of the heartbeat location determination are satisfactory. The determination of satisfaction may be a function of one or more clinical factors. For example, in one embodiment the determination may be based on whether a total number of heartbeats detected is within an expected range of values. For example, a normal resting individual may have a heart beat period of 0.5 seconds=120 beats/minute, along with an average time-between-beats of less than 2 seconds. If the number of heartbeats detected lies within the expected range, then the results may be satisfactory and the method 400 is complete. However, if the results are not satisfactory, e.g., the number of heartbeats lies outside the expected range, then the method 400 may proceed to 470.

In addition to the clinical factors, there may be statistical factors which indicate whether detection parameters, such as the list of remaining coefficients, should be revised. One statistical factor is missing beats, which may be indicated by a change in the number of beats detected. For example, if beats were previously occurring once per second and now occur once every two seconds, this may indicate that beats are missing, e.g., being underreported.

In 470, an additional coefficient may be added to the remaining coefficients. For instance, if the addition is being performed for the first time, the remaining coefficients may only include the highest row of coefficients plus a coefficient from the next highest row. The method 400 then returns to 440, where an inverse wavelet transform may be performed using the remaining coefficients. In this manner, additional coefficients may be added to the remaining coefficients until a result of a heartbeat location detection is satisfactory.

Figure 14:
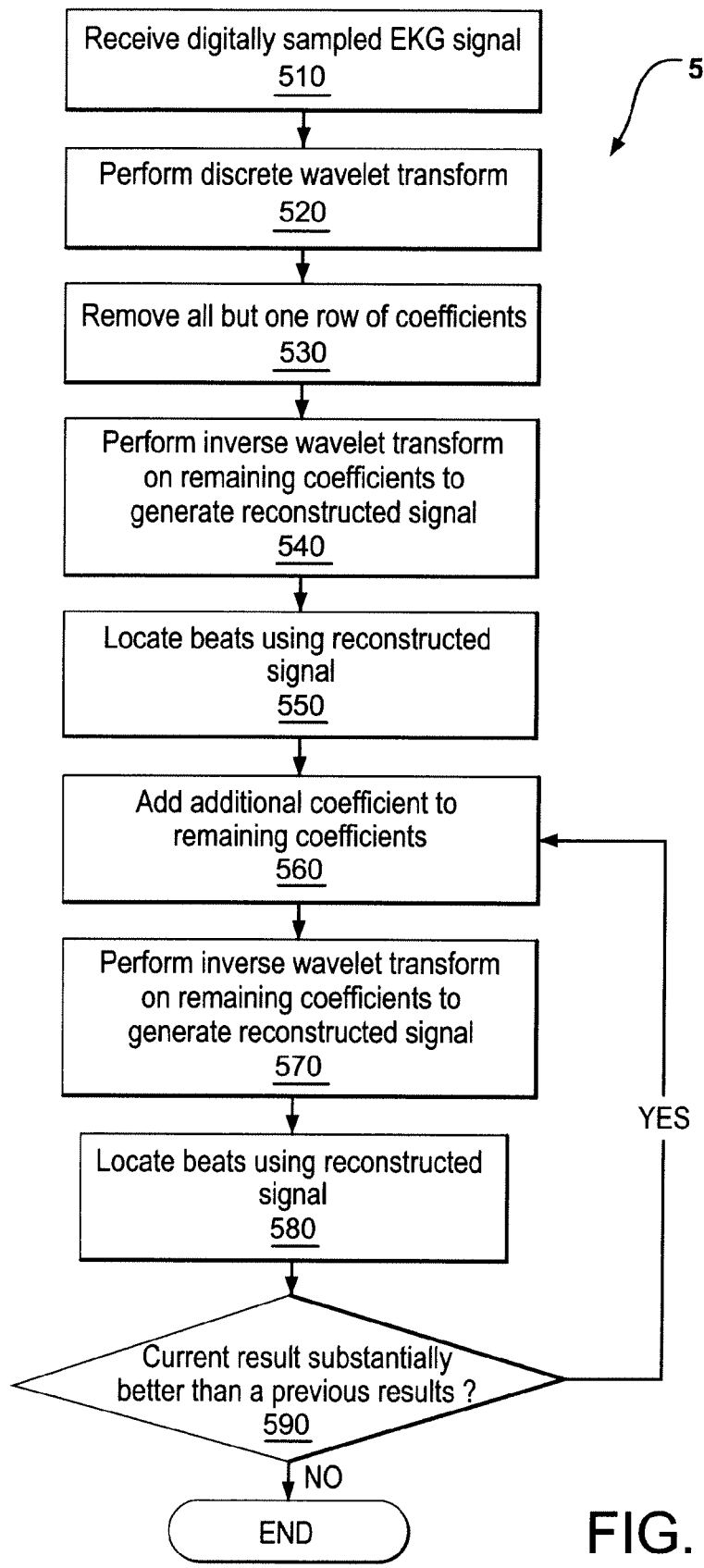
FIG. 14 shows an example of another method for selecting wavelet coefficients according to an example embodiment of the present invention.

FIG. 14 shows an example of a method 500 for selecting coefficients according to an example embodiment of the present invention. The method 500 may initially proceed in a manner similar to that of steps 410 to 450 of the method 400. For example, in 510, a digitally sampled EKG signal may be received. In 520, a discrete wavelet transform may be performed on the EKG signal. In 530, all but one row of coefficients, e.g., the highest value or the highest frequency coefficients, may be removed. In 540, an inverse wavelet transform may be performed on the remaining coefficients to generate a reconstructed signal. In 550, heartbeats may be located using the reconstructed signal.

In 560, an additional coefficient may be added to the remaining coefficients. The additional coefficient may be added based on frequency or value. In 570, an inverse wavelet transform may be performed using the remaining coefficients to generate a reconstructed signal. In 580, heartbeat locations may be located on the reconstructed signal.

In 590, a determination of whether the result of a current heartbeat location determination is substantially better than a previous result may be performed. The determination may be a function of one or more clinical factors. For example, the total number of heartbeats detected in the current result may be compared to the number of heartbeats detected in a previous result. Initially, using few coefficients may result in under-reporting. As coefficients are added, more heartbeats may be detected. Thus, if the current result shows an increase in the number of heartbeats, this may be an indication that the current result is substantially better. However, if too many coefficients are added, there may be over-reporting. This may be due to the presence of low frequency or low value coefficients associated with noise, which may be confused with actual heartbeats. Thus, a stop condition may be included in the definition of what constitutes a substantial improvement according to the present invention.

In one embodiment, the stop condition may be a function of a rate of change in the number of heartbeats detected. Initially, the change rate may be high, but as coefficients are added, the change rate may begin to slow. Thus, a plateau in the change rate may define a stop condition. In another embodiment, the stop condition may be a function of whether the number of heartbeats detected lies within an expected range of values. The stop condition may not be imposed until the number of heartbeats detected is near or exceeds the expected range.

The current result may only be compared to an immediately preceding result. Alternatively, in other embodiments, the current result may be compared to a plurality of previous results to determine a general trend in the results. If the current result is not substantially better, then the method 500 is complete. However, if the current result is substantially better, the method 500 may return to 560, where an additional coefficient may be added to the remaining coefficients. In this manner, additional coefficients may be added to the remaining coefficients until a result of a heartbeat location determination no longer provides a substantial improvement over a previous result.

Although the methods 400 and 500 were described with reference to iterative techniques in which a single coefficient was added during each iteration, it may also be possible to add a plurality of coefficients at each iteration. For example, coefficients may be added in groups based on, e.g., similar value or similar frequency. Similarly, an initial set of remaining coefficients need not be limited to a single row of coefficients, but may include any number of coefficients, e.g., a set of rows comprising the highest value or highest frequency coefficients.

Figure 15:
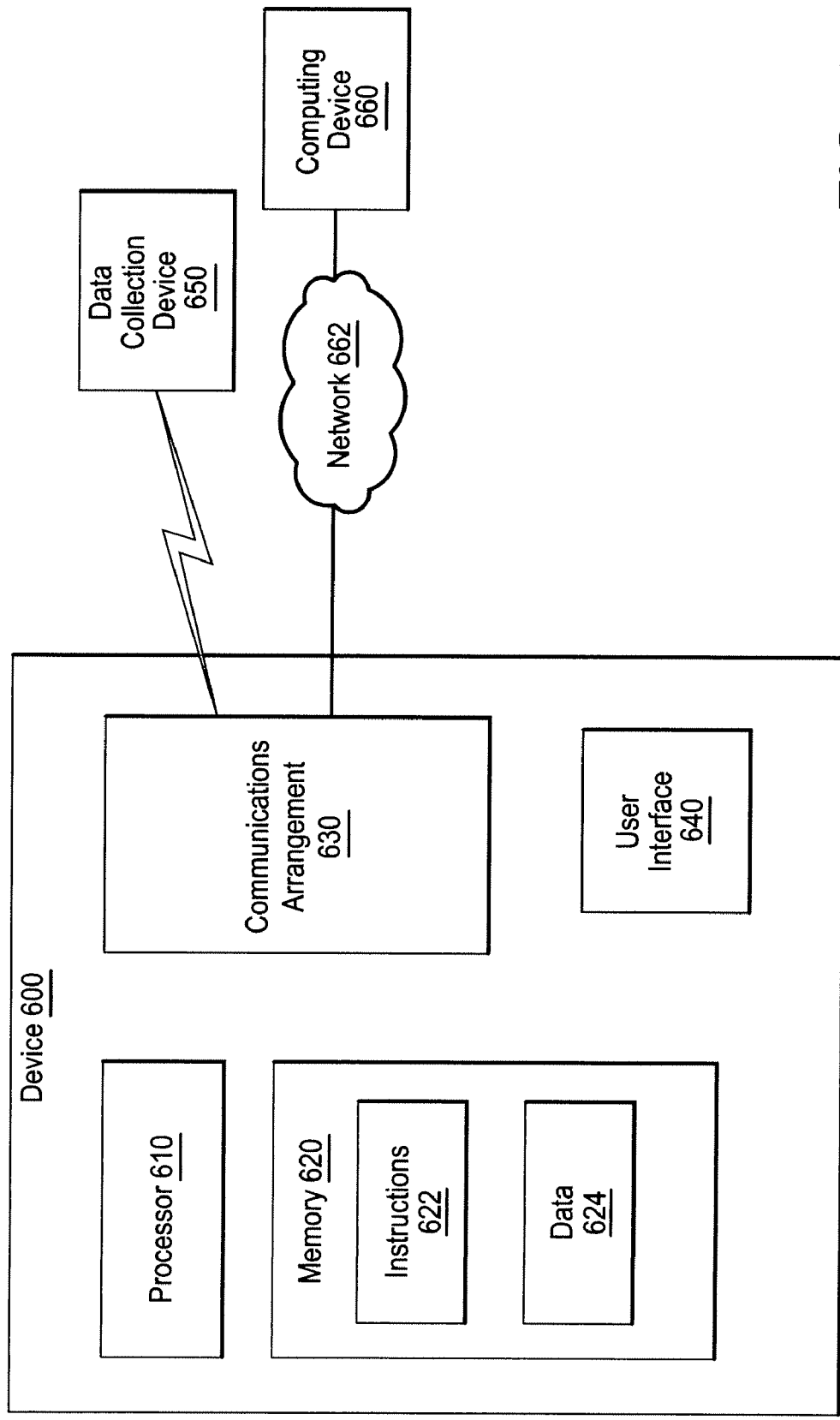
FIG. 15 shows an example of a system for detecting bio signal features in the presence of noise according to an example embodiment of the present invention.

FIG. 15 shows an example of a system for detecting bio signal features (heartbeats) in the presence of noise according to an example embodiment of the present invention. The system may include a device 600, which may include a processor 610, a memory 620, a communications arrangement 630 and a user interface 640. The device 600 may be configured to perform any of the methods 100, 200, 300, 400 and 500 previously described. In particular, the processor 610 may be configured to execute instructions 622 located in the memory 620. The instructions 622 may include instructions for detecting heartbeats and selecting wavelet coefficients according to the methods 100 to 500. The processor 610 may include a microprocessor, an integrated circuit or series of integrated circuits, analog, digital, and other hardware components.

The memory 620 may be a computer-readable medium including any type of readable or writable memory, include RAM, ROM, flash memory, an optical or electromagnetic drive, a compact disc, etc. In addition to storing the instructions 622, the memory 620 may also include data 624 used in performing any of the previously described methods 100 to 500. For example, the data 624 may include digital values, e.g., x-y coordinates, corresponding to an EKG signal. The data 624 may also include a workspace for storing wavelet transform coefficients, reconstructed signals, derivative signals, thresholding signals, length transform data, remaining coefficients, and removed coefficients.

The communications arrangement 630 may include any combination of hardware or software components for communicating with a data source such as a data collection device 650 or a computing device 660. The data source may be configured to collect the digital signal and transmit it to the device 100 via the communications arrangement 630. The communications arrangement 630 may be in wired and/or wireless communication with the data source. For example, the communications arrangement 630 may wirelessly communicate with the device 650. The communications arrangement 630 may also be in wired communication with the device 660 via a network 662, which may be a local area network, a wide area network, a telephone network, the Internet, etc.

Data may be collected and transmitted to the device 600 in substantially real time. For example, the device 650 may include sensor electrodes for generating EKG signals. An analog EKG signal may be processed and converted into a digital signal, then transmitted. Data collection may also be done any time after the analog signal is recorded. For example, analog or digital signals may be stored in a database on the device 660, batch processed, and transmitted together. The device 660 may, similar to the device 650, include sensors for measuring EKG signals. Alternatively, the device 660 may be configured to communicate with an external sensing device. In further embodiments, data may be transmitted to the device via manual input, a storage device such as a CD-ROM, or any other input arrangement.

It will be appreciated that the example system, device and methods described above may be integrated into a system for monitoring patient health. An example of a system which may be suitable for use with the present invention is described in U.S. patent application Ser. No. 11/938,409, titled Method and System for Active Patient Management, filed Nov. 12, 2007, and which describes an active patient management system for monitoring patient EKG signals along with other health indicators. In one embodiment, one or more of the methods 100 to 500 may be implemented in the active patient management system as a software program stored in a computer-readable medium such as hard drive memory, flash memory, floppy disk memory, optically-encoded memory (e.g., a compact disk, DVD-ROM, DVD±R, CD-ROM, CD±R, holographic disk), a thermomechanical memory (e.g., scanning-probe-based data-storage), or any type of machine-readable (computer-readable) storage medium.

In the preceding specification, the present invention has been described with reference to specific example embodiments thereof. It will, however, be evident that various modifications and changes may be made thereunto without departing from the broader spirit and scope of the present invention as set forth in the claims that follow. The specification and drawings are accordingly to be regarded in an illustrative rather than restrictive sense.

The invention claimed is:

1. A computer-based method for detecting features in a digitally sampled biological (bio) signal, comprising:
   applying a wavelet transform to the bio signal to generate a list of wavelet transform coefficients;
   ranking the coefficients according to value;
   removing at least one low value coefficient;
   performing an inverse wavelet transform using the remaining coefficients to generate a reconstructed signal; and
   detecting feature locations using the reconstructed signal.

2. The method of claim 1, further comprising:
   applying a length transform; and
   detecting feature locations from an output of the length transform.

3. The method of claim 2, wherein the length transform is applied to the reconstructed signal.

4. The method of claim 2, wherein the length transform is applied to a mathematical derivative of the reconstructed signal.

5. The method of claim 1, wherein the feature locations are detected by locating a peak maximum.

6. The method of claim 2, wherein the feature locations are detected by:
   determining a maximum value of the length transform output;
   locating a first point in a left portion of a peak pulse of the length transform output and a second point in a right portion of the peak pulse, the first and second points being equal in value, the value being a function of the maximum value; and
   detecting feature locations from the length transform output by calculating a location halfway between the first and second points.

7. The method of claim 6, wherein the function corresponds to half of the maximum value.

8. The method of claim 2, further comprising:
   rectifying an input of the length transform.

9. The method of claim 2, further comprising:
   selecting a window size of the length transform as a function of a known feature duration.

10. The method of claim 1, further comprising:
    prior to the step of detecting, removing baseline drift from the bio signal.

11. The method of claim 1, further comprising:
    initially removing all but a set of highest value coefficients;
    determining whether a result of a current detection is satisfactory; and
    if the result is unsatisfactory, repeating the steps of adding a next highest coefficient to the remaining coefficients, performing the inverse wavelet transform, and detecting until the result is satisfactory.

12. The method of claim 11, wherein the determination of satisfaction is based on whether a number of features detected is within a range of expected values.

13. The method of claim 11, wherein the determination of satisfaction is based on whether a change occurs in a detected feature rate over time.

14. The method of claim 1, further comprising:
    initially removing all but a set of highest value coefficients;
    adding a next highest coefficient to the remaining coefficients;
    repeating the steps of performing the inverse wavelet transform and detecting;
    determining whether a result of a current detection is a substantial improvement compared to a result of a previous detection; and
    if the current result is a substantial improvement, repeating the steps of adding a next highest coefficient, performing the inverse wavelet transform, and detecting until a result of the current detection no longer yields a substantial improvement compared to a previous detection.

15. The method of claim 14, wherein the determination of improvement is based on a rate of change in a number of features detected when an additional coefficient is added.

16. The method of claim 1, wherein the bio signal is an electrocardiogram signal and the features are heartbeats.

17. A computer-based method for detecting features in a digitally sampled biological (bio) signal, comprising:
applying a wavelet transform to the bio signal to generate a list of wavelet transform coefficients;
ranking the coefficients according to frequency;
removing at least one low frequency coefficient;
performing an inverse wavelet transform using the remaining coefficients to generate a reconstructed signal; and
detecting feature locations using the reconstructed signal.

18. The method of claim 17, wherein the feature locations are detected by locating a peak maximum.

19. The method of claim 17, further comprising:
filtering the reconstructed signal through a low pass filter; and
detecting feature locations from the filtered signal.

20. The method of claim 19, wherein the feature locations are detected by:
determining a maximum value of the filtered signal;
locating a first point in a left portion of a peak pulse of the filtered signal and a second point in a right portion of the peak pulse, the first and second points being equal in value, the value being a function of the maximum value; and
detecting feature locations from the filtered signal by calculating a location halfway between the first and second points.

21. The method of claim 20, wherein the function corresponds to half of the maximum value.

22. The method of claim 19, further comprising:
rectifying the reconstructed signal prior to filtering.

23. The method of claim 19, further comprising:
rectifying the filtered signal after filtering.

24. The method of claim 17, further comprising:
initially removing all but a set of highest frequency coefficients;
determining whether a result of a current detection is satisfactory; and
if the result is unsatisfactory, repeating the steps of adding a next highest coefficient to the remaining coefficients, performing the inverse wavelet transform, and detecting feature locations until the result is satisfactory.

25. The method of claim 24, wherein the determination of satisfaction is based on whether a number of features detected is within a range of expected values.

26. The method of claim 24, wherein the determination of satisfaction is based on whether a change occurs in a detected feature rate over time.

27. The method of claim 17, further comprising:
initially removing all but a set of highest frequency coefficients;
adding a next highest coefficient to the remaining coefficients;
repeating the step of detecting feature locations;
determining whether a result of a current detection is a substantial improvement compared to a result of a previous detection; and
if the current result is a substantial improvement, repeating the steps of adding a next highest coefficient, performing an inverse wavelet transform, and detecting until a result of the current detection no longer yields a substantial improvement compared to a previous detection.

28. The method of claim 27, wherein the determination of improvement is based on a rate of change in a number of features detected when an additional coefficient is added.

29. The method of claim 17, wherein the bio signal is an electrocardiogram signal and the features are heartbeats.

30. A device for detecting features in a digitally sampled biological (bio) signal, comprising:
a communications arrangement configured to receive the bio signal;
a processor; and
a memory including instructions configuring the processor to:
apply a wavelet transform to the bio signal to generate a list of wavelet transform coefficients;
rank the coefficients according to value;
remove at least one low value coefficient;
perform an inverse wavelet transform using the remaining coefficients to generate a reconstructed signal; and
detect feature locations using the reconstructed signal.

31. A device for detecting features in a digitally sampled biological (bio) signal, comprising:
a communications arrangement configured to receive the bio signal;
a processor; and
a memory including instructions configuring the processor to:
apply a wavelet transform to the bio signal to generate a list of wavelet transform coefficients;
rank the coefficients according to frequency;
remove at least one low frequency coefficient;
perform an inverse wavelet transform using the remaining coefficients to generate a reconstructed signal; and
detect feature locations using the reconstructed signal.

32. A computer-readable medium having stored thereon a series of instructions executable by a processor for detecting features in a digitally sampled biological (bio) signal, the instructions configured to cause the processor to perform the steps of:
applying a wavelet transform to the bio signal to generate a list of wavelet transform coefficients;
ranking the coefficients according to value;
removing at least one low value coefficient;
performing an inverse wavelet transform using the remaining coefficients to generate a reconstructed signal; and
detecting feature locations using the reconstructed signal.

33. A computer-readable medium having stored thereon a series of instructions executable by a processor for detecting features in a digitally sampled biological (bio) signal, the instructions configured to cause the processor to perform the steps of:
applying a wavelet transform to the bio signal to generate a list of wavelet transform coefficients;
ranking the coefficients according to frequency;
removing at least one low frequency coefficient;
performing an inverse wavelet transform using the remaining coefficients to generate a reconstructed signal; and
detecting feature locations using the reconstructed signal.

* * * * *